United States Patent [19]

Harmar et al.

[11] Patent Number: 5,268,359
[45] Date of Patent: Dec. 7, 1993

[54] HUMAN TACHYKININS AND THEIR PRECURSOR

[75] Inventors: Anthony J. Harmar, Edinburgh, Scotland; John Pascall, Newmarket; Ann McKeown, Locks Heath, both of England

[73] Assignee: Medical Research Council, London, England

[21] Appl. No.: 285,964

[22] PCT Filed: Jun. 3, 1987

[86] PCT No.: PCT/GB87/00382

§ 371 Date: Dec. 5, 1988

§ 102(e) Date: Dec. 5, 1988

[87] PCT Pub. No.: WO87/07643

PCT Pub. Date: Dec. 17, 1987

[30] Foreign Application Priority Data

Jun. 3, 1986 [GB] United Kingdom ............... 8613431

[51] Int. Cl.$^5$ ................ A61K 37/02; C07K 13/00
[52] U.S. Cl. ............................. 514/13; 514/2; 514/12; 514/21; 530/324; 530/326; 930/10

[58] Field of Search ............... 514/12, 13, 2, 21; 530/324, 399, 236

[56] References Cited

PUBLICATIONS

Tatemoto et al, *Chemical Abstracts*, 103, No. 5, 1985, p. 53, abst. No. 32420y.
Nawa et al, *Nature*, 306, 32–36, 1983.
Harmer et al., *FEBS* Letters, 208, No. 1, Nov. 1986, pp. 67–72.

*Primary Examiner*—F. T. Moezie
*Attorney, Agent, or Firm*—John P. White

[57] ABSTRACT

A DNA has the nucleotide sequence shown in FIG. 1. The derived amino acid sequence is also shown in FIG. 1. Novel polypeptides have the amino acid sequence corresponding to amino acids 1 to 126, 20 to 56 and 111 to 126 shown in FIG. 1 and may be prepared by culturing a host organism in which the DNA includes the relevant segment of DNA cut from the nucleotide sequence shown in FIG. 1.

2 Claims, 10 Drawing Sheets

```
Bovine          C      C   C∇G AT   A ΔCC G    G
Human    GAGAGTGCGGGAGCCGACCACGTGCCTCGGAGGAACCAGAGAAACTCAGCCCCGCGGGA
         1       ----+----+----+----+----+----+----+----+----+----+----+

Bovine   GG   A CT  G           G               GA     T CA
Human    CTGTCCGTCGCAAACATGAAAATCCTCGTGGCCTTGGCAGTCTTTTTCTTGTC
         61  ----+----+----+----+----+----+----+----+----+----+----+
Human                     MetLysIleLeuValAlaLeuAlaValPhePheLeuVal
Bovine                                               Val    Ile  Phe Ile Bovine        A    C            C           C       TC  T
Human    TCCACTCAGCTGTTTGCAGAAGAAATAGGAGCCAATGATGATCTGAATTACTGGTCCGAC
         121 ----+----+----+----+----+----+----+----+----+----+----+
Human    SerThrGlnLeuPheAlaGluGluIleGlyAlaAsnAspAspLeuAsnTyrTrpSerAsp
Bovine   Ser                                                    Phe
```

FIG. 1-1

```
Bovine                       C                    A           C
Human    TGGTACGACAGCGACCAGATCAAGGAGGAAACTGCCGGAGCCCTTTGAGCATCTTCTGCAG
  181    ------+---------+---------+---------+---------+---------+
Human    TrpTyrAspSerAspGlnIleLysGluGluLeuProGluProPheGluHisLeuLeuGln
Bovine   Ser                        Met Bovine                 T                           G
Human    AGAATCGCCCGAGACCCAAGCCTCAGCAGTTCTTTGGATTAATGGGCAAACGGGATGCT
  241    ------+---------+---------+---------+---------+---------+
Human    ArgIleAlaArgArgProLysProGlnGlnPhePheGlyLeuMetGlyLysArgAspAla
Bovine
```

FIG. 1-2

```
Bovine                        G                              C
Human   GATTCCTCAATTGAAAAACAAGTGGCCCCTGTTAAAGGCTCTTTATGGACATGGCCAGATC
301     ----+----+----+----+----+----+----+----+----+----+----+----+
Human   AspSerSerIleGluLysGlnValAlaLeuLeuLysAlaLeuTyrGlyHisGlyGlnIle
Bovine                                                             Leu Bovine                    G
Human   TCTCACAAAAGACATAAAACAGATTCCTTTGTTGGACTAATGGGCAAAAGAGCTTTAAAT
361     ----+----+----+----+----+----+----+----+----+----+----+----+
Human   SerHisLysArgHisLysThrAspSerPheValGlyLeuMetGlyLysArgAlaLeuAsn
Bovine
```

FIG. 1-3

```
                         TG           G                   A            G
Bovine   TCTGTGGCTTATGAAAGGAGTGCAATGCAGAATTATGAAAGAAGACGTTAATAAACTACC
Human    ----+---------+---------+---------+---------+---------+
421
Human    SerValAlaTyrGluArgSerAlaMetGlnAsnTyrGluArgArgArgEND
Bovine                         Val              Asp            Lys Bovine        △
         TAACATTATTTATTCAGCTTCATTTGTCAATGGGCAATGACACAGGTAAATTAAGACATG
Human    ----+---------+---------+---------+---------+---------+
481
```

FIG. 1-4

```
                                 TTG       T A   T  C     G
Bovine
Human  CACTATGAGGAATAATTATTTAATAACAATTGTTAGGGTTGAAAATTCAAAAGT
 541   ----------+---------+---------+---------+---------+

G    A G           AAA  A      G    T C  C
Bovine A
Human  GTTTATTTTTCATATTGTGCCAATATGTTATTGTAAACATGTGTTTAATTCCAATATGAT
 601   ----------+---------+---------+---------+---------+---------+

G                     C      A         CC           C      G
Bovine A  AG C▽ G
Human  GACTCCCTTAAAATAGAAATAAGTGTTATTTCTCAACAAAGCACAGTGTTAAATGAAAT
 661   ----------+---------+---------+---------+---------+---------+
```

FIG. 1-5

```
             A
             ▽   A  G  A     T  T  T  C  ΔC     GG
Bovine       TGTAAACCTGTCAATGATACAGTCCCTAAAGAAAAAATCATTGCTTTGAAGCAGTTG
Human    ----+---------+---------+---------+---------+---------+----
721

A              TTCTG
             A  ΔT  G  A  A     T  ▽AT T  ΔG       ▲T       C   Δ
Bovine       TGTCAGCTACTGCGGAAAAGGAAACTCCTGACAGTCTTGTGCTTTCCTATTTGTT
Human    CA  ----+---------+---------+---------+---------+---------+----
781

ΔG              G     CA     G         C   C
Bovine       TTCATGGTGAAAATGTACTGAGATTTGGTATTACACTGTATTTGTATCTCTGAAGCATG
Human    ----+---------+---------+---------+---------+---------+----
841
```

FIG. 1-6

```
                                      ΔCA   A          T C          G  Δ
Bovine
Human  TTTCATGTTTTGTGACTATATAGAGATGTTTTTAAAAGTTTCAATGTGATTCTAATGTCT
 901   ------+---------+---------+---------+---------+---------+

Bovine  Δ   T    CA             A    T                     G
Human   TCATTTCATTGTATGATGTGTTGTGATAGCTAACATTTTTAAATAAAGAAAAATATCTT
 961    ------+---------+---------+---------+---------+---------+

Bovine  Δ
Human   G  -
 1021
```

HUMAN TACHYKININS AND THEIR PRECURSOR

BACKGROUND OF THE INVENTION

1. Field of the Invention

The present inventions relates to human tachykinins, their precursors and their production by recombinant DNA technology.

The abbreviations used herein are as follows:
b—bovine
h—human
PPT—preprotachykinin
EDTA—ethylene diamine tetracetic acid
BSA—bovine serum albumin
PVP—polyvinyl pyrrolidone
SDS—sodium dodecyl sulphate
SSC—saline sodium citrate.

2. Description of Related Art Including Information Disclosed under 35 C.F.R. §§1.97-1.99.

The tachykinins are a family of small peptides, present in the brain and peripheral tissues, which play important roles as neurotransmitters and as hormones. The tachykinins are characterised by a common C-terminal amino acid sequence, -Phe-X-Gly-Leu-Met-NH$_2$, wherein X is a hydrophobic or aromatic residue [Erspamer, V., Trends in Neuroscience, 4, 267-269, 1981].

The first tachykinin found in mammals is known as substance P, which is though to be involved in the transmission of painful stimuli in the spinal cord. It is also released from sensory nerves in the skin and is thought to play a role in the inflammatory response.

Subsequently, other tachykinins, known as neurokinin A and neurokinin B were reported [Kimura, S., Oada, M., Sugita, Y., Kanazawa, I. and Munekata, E., Proc Jap. Acad. Series B, 59, 101-104, 1983], and it has recently been shown [Tatemoto, K., Lundberg, J. M., Jornvall, H and Mutt, V., Biochem. Biophys. Res. Comm., 128, 947-953, 1985] that in the porcine central nervous system, there is a larger tachykinin, known as neuropeptide K.

It has been shown [Nawa, H., Hirose, T., Takashima, H., Inayama, S. and Nakanishi, S., Nature, 306, 32-36, 1983] that in bobine brain substance P is derived from one of two larger polypeptide precursors, known as alpha- and beta-bovine preprotachykinin (bPPT). It has been shown that the mRNAs encoding alpha- and beta-bPPTs are derived from a single bPPT gene as a result of tissue specific RNA splicing [Nawa, H., Kotani, H and Nakanishi, S., Nature 312, 729-734, 1984]. It has been shown that bovine neurokinin A is derived from beta-bPPT but cannot be derived from alpha-bPPT.

Thus, it has been shown that residues 58 to 68 and 98 to 107 of beta-bPPT correspond to bovine substance P and bovine neurokinin A. Moreover it has been shown that residues 72 to 107 correspond to the sequence of bovine neuropeptide K.

SUMMARY OF THE INVENTION

The present invention is based on the observation that certain human carcinoid tumours may produce large quantities of ectopic substance P and that these tumour cells might therefore provide a source of human substance P mRNA. During this investigation, it was discovered that human substance P was part of a precursor polypeptide similar to bovine beta-PPT. This polypeptide is referred to herein as hPPT. The existence of a human (h) PPT polypeptide had not previously been demonstrated. hPPT mRNA was discovered to be closely homologous to beta-bPPT mRNA, and it was therefore appreciated that this could provide a source not only of human substance P, but also of other human tachykinins.

Therefore the present invention provides human PPT, human tachykinins derived therefrom, cDNA sequences coding therefor, plasmids containing these sequences, and methods for their production using recombinant DNA technology.

BRIEF DESCRIPTION OF THE DRAWINGS

FIG. 1 shows a human DNA sequence containing nucleotides numbered 1 to 1021.

DESCRIPTION OF THE PREFERRED EMBODIMENTS

The present inventors have discovered that a human PPT gene encodes a human PPT polypeptide which contains sequences identical to bovine substance P and neuropeptide K and porcine neurokinin A.

Therefore the present invention provides a DNA consisting of or containing the human nucleotide sequence 1 to 1021 as shown in FIG. 1, a DNA consisting of or containing the human nucleotide sequence 1 to 260 as shown in FIG. 1 and a DNA consisting of or containing the human nucleotide sequence 148 to 1021 as shown in FIG. 1.

The invention also provides fragments of the DNA sequences defined above.

Further, the present invention provides a DNA containing the nucleotide sequence coding for a polypeptide having the following amino acid sequence:

Glu—Glu—Ile—Gly—Ala—Asn—Asp—Asp—Leu—Asn—

Tyr—Trp—Ser—Asp—Trp—Tyr—Asp—Ser—Asp—Gln—

Ile—Lys—Glu—Glu—Leu—Pro—Glu—Pro—Phe—Glu—

His—Leu—Leu—Gln—Arg—Ile—Ala.

Preferably, the DNA contains the nucleotide sequence coding for the polypeptide having the following amino acid sequence:

Ala—Leu—Asn—Ser—Val—Ala—Tyr—Glu—Arg—Ser—
Ala—Met—Gln—Asn—Tyr—Glu.

In another embodiment of the invention the DNA contains the nucleotide sequence coding for the polypeptide having the following amino acid sequence:

Met—Lys—Ile—Leu—Val—Ala—Leu—Ala—Val—Phe—

Phe—Leu—Val—Ser—Thr—Gln—Leu—Phe—Ala—Glu—

Glu—Ile—Gly—Ala—Asn—Asp—Asp—Leu—Asn—Tyr—

Trp—Ser—Asp—Trp—Tyr—Asp—Ser—Asp—Gln—Ile—

Lys—Glu—Glu—Leu—Pro—Glu—Pro—Phe—Glu—His—

Leu—Leu—Gln—Arg—Ile—Ala—Arg—Arg—Pro—Lys—

Pro—Gln—Gln—Phe—Phe—Gly—Leu—Met—Gly—Lys—

Arg—Asp—Ala—Asp—Ser—Ser—Ile—Glu—Lys—Gln—

-continued

Val—Ala—Leu—Leu—Lys—Ala—Leu—Tyr—Gly—His—

Gly—Gln—Ile—Ser—His—Lys—Arg—His—Lys—Thr—

Asp—Ser—Phe—Val—Gly—Leu—Met—Gly—Lys—Arg—

Ala—Leu—Asn—Ser—Val—Ala—Tyr—Glu—Arg—Ser—

Ala—Met—Gln—Asn—Tyr—Glu.

The present invention also provides transformants in which the DNA contains the nucleotide sequence 1 to 1021 as shown in FIG. 1, or the nucleotide sequence 1 to 260 as shown in FIG. 1 or the nucleotide sequence 148 to 1021 as shown in FIG. 1.

Preferably the host of the transformant is *Escherichia coli.*

Preferably the transformant is *Escherichia coli* harbouring the plasmid ph 8.216 (Deposition Number NCTC 12096).

The invention also provides a transformant comprising *Escherichia coli* harbouring the plasmid phE293 (Deposition Number NCTC 12097).

The said transformants have been deposited with the National Collection of Type Cultures, London on Jun. 3, 1987.

The invention further provides a vector comprising a DNA segment as defined above, said segment being oriented within said vector such that in a host said segment is expressed to produce a polypeptide.

In addition the invention provides a host organism transformed by the said vector.

According to the invention there is also provided a method of preparing a polypeptide, comprising culturing the host organism aforesaid and isolating the polypeptide from the culture.

The present invention further provides the following novel polypeptides:

(i) the polypeptide, beta-preprotachykinin (1-126), having the amino acid sequence:

Met—Lys—Ile—Leu—Val—Ala—Leu—Ala—Val—Phe—

Phe—Leu—Val—Ser—Thr—Gln—Leu—Phe—Ala—Glu—

Glu—Ile—Gly—Ala—Asn—Asp—Asp—Leu—Asn—Tyr—

Trp—Ser—Asp—Trp—Tyr—Asp—Ser—Asp—Gln—Ile—

Lys—Glu—Glu—Leu—Pro—Glu—Pro—Phe—Glu—His—

Leu—Leu—Gln—Arg—Ile—Ala—Arg—Arg—Pro—Lys—

Pro—Gln—Gln—Phe—Phe—Gly—Leu—Met—Gly—Lys—

Arg—Asp—Ala—Asp—Ser—Ser—Ile—Glu—Lys—Gln—

Val—Ala—Leu—Leu—Lys—Ala—Leu—Tyr—Gly—His—

Gly—Gln—Ile—Ser—His—Lys—Arg—His—Lys—Thr—

Asp—Ser—Phe—Val—Gly—Leu—Met—Gly—Lys—Arg—

Ala—Leu—Asn—Ser—Val—Ala—Tyr—Glu—Arg—Ser—

Ala—Met—Gln—Asn—Tyr—Glu;

(ii) the polypeptide beta-preprotachykinin (20-56) having the amino acid sequence:

Glu—Glu—Ile—Gly—Ala—Asn—Asp—Asp—Leu—Asn—

-continued

Tyr—Trp—Ser—Asp—Trp—Tyr—Asp—Ser—Asp—Gln—

Ile—Lys—Glu—Glu—Leu—Pro—Glu—Pro—Phe—Glu—

His—Leu—Leu—Gln—Arg—Ile—Ala, and;

(iii) the polypeptide, beta-preprotachykinin (111-126), having the amino acid sequence:

Ala—Leu—Asn—Ser—Val—Ala—Tyr—Glu—Arg—Ser—
Ala—Met—Gln—Asn—Tyr—Glu.

It is to be understood that the invention also includes fragments of the polypeptides (i) to (iii) defined above which maintain the same or similar biological effect as the whole defined sequence.

The present invention will now described by way of illustration only, in the following Example.

A metastatic deposit from a human laryngeal carcinoid tumour was obtained by biospy. This was shown to contain approximately 1 microgram/g (wet weight) of substance P-like activity by immunoreactivity [Harmar, A. J., Armstrong, A., Lee C-M. and Emson, P. C., Brain Res., 323, 342-344, 1984]. The tumour was associated with hypersalivation and local pain, possibly caused by ectopic substance P production [Going, J. J., Harmar, A. J., Gow, I. F. and Edwards, C. R. W., J. Endocrin., 104, 52, 1985].

Poly (A)+RNA was obtained from 3.5 g of tumour tissue (stored at −70° C.) using the guanidine thiocyanate procedure [Chirgwin, J. M., Przybyla, A. E., MacDonald, R. J., and Rutter, W. J., Biochem., 18, 5294-5299, 1979] and chromatography on oligo (dT) cellulose [Aviv, H and Leder, P., PNAS USA, 69, 1408-1412, 1972]. The first strand of double stranded cDNA was synthesised using an oligo $(dT)_{12-18}$ primer [Craig, R. K., Hall, L., Parker, D. and Campbell, P. N., Biochem J., 194, 989-998, 1981], following which the second strand was synthesised using a different procedure [Gubler, V. and Hoffmann, B. J., Gene, 25, 263-269, 1983]. The double stranded DNA was tailed with approximately 25 dC residues using terminal deoxynucleotidyl transferase as described by its suppliers (Bethesda Research Laboratories).

The poly (dC)-tailed cDNA and poly (dG)-, PstI-restricted pBR322 DNA (supplied by New England Nuclear) was annealed [Peacock, S. L., McIver, C. M. and Monahan, J. J., Biochem. Biophys. Acta, 655, 243-250, 1981] at final concentrations of 8 ng/ml and 400 ng/ml respectively. The resulting chimeric plasmids were then used to transform the *E. coli* strain RR1 [Dagent, M. and Ehrlich, S. D., Gene, 6, 23-28, 1979].

Aliquots of the transformed cells were plated onto 1% w/w agar in L-broth containing 10 micrograms/ml tetracycline and incubated overnight at 37° C. Tetracycline-resistant colonies were then picked in triplicate onto Biodyne (Trade Mark) filters overlying agar and allowed to grow overnight at 37° C. prior to storage or filter hybridisation.

To identify clones containing cDNA sequences coding for human substance P, 8,700 tetracycline-resistant transformants grown on the Biodyne filters were screened using a synthetic heptadecamer oligonucleotide probe having the sequence

```
             C   A
5'-TTTGCCCAT A  TCCAA-3'.
             T   G
```

This heptadecamer sequence is complementary to the coding sequences in the beta-bPPT gene which encode the common amino acid sequences in bovine substance P and bovine neurokinin A.

In the screening, the bacteria were lysed and the DNA was fixed onto the filters [Grunstein, M. and Hogness, D. S., PNAS USA, 72, 3961-3965, 1975]. The filters were prehybridised for 18 h at 37° C. in a solution containing 0.9M NaCl, 60 mM EDTA, 19.8 mM Tris Hcl, pH8, 5×Denhardt's reagent (0.1% each of DSA, PVP and Ficoll), 0.1% SDS and 5% dextran suplhate. After prehybridisation, the buffer was discarded and replaced by an identical solution containing heat denatured hybridisation probe labelled at the 5' end with [gamma$^{32P}$]-ATP using polynucleotide kinase [Maxam, A. M. and Gilbert, W., Meth Enzymol., 65, 499-560, 1980].

The filters were allowed to hybridise for 18 h at 37° C. and were then washed five times (30 minutes per wash) with 6×SSC (0.9M NaCl, 0.09M sodium citrate, pH7) at room temperature and twice with 6×SSC containing 0.1% SDS at 35° C.

The Filters were then dried and exposed to Kodak X-Omat S film for 24 to 72 hours using Kodak X-Omatic intensifying screens.

A single weakly positive colony (phE293) was identified following the screening procedure. Moreover, on rescreening the clone library following chloramphenicol amplification of the plasmid DNA, this colony was strongly positive.

The sequence of both strands of the insert in phE293 was determined by isolation of fragments thereof using restriction enzymes of fragments thereof using restriction enzymes PstI, Bgl II, RsaI and AluI. The fragments were subcloned into phages M13mp18 or M13mp19 and were sequenced using standard techniques [Sanger, F., Nicklen, S. and Coulson, A. R., PNAS USA, 74, 5463-5467, 1977]. The sequence thus obtained of 874 base pairs, of which 321 base pairs of sequence encode polypeptide, the remaining base pairs comprising a 3'-untranslated region. The phE293 sequence comprises nucleotides 148 to 1021 of the sequence shown in FIG. 1.

The amino acid sequence corresponding to the coding sequence is shown below the nucleotide sequence in FIG. 1. Above the nucleotide sequence is shown where the sequence for bovine beta-PPT cDNA differs from the phE293 insert sequence, and below the amino acid sequence is shown where the sequence for bovine beta-PPT polypeptide differs from the amino acid sequence encoded by the phE293 insert sequence. Homology between the human and bovine sequences was maximised by inserting gaps indicated by triangular symbols.

Also indicated in FIG. 1 are the expected positions of the substance P (nucleotides 265 to 297) and neurokinin A (nucleotides 385 to 414) sequences. These sequences correspond to the known sequences for these peptides and in particular include the characteristic C-terminal sequence. Moreover, the polypeptide sequence also includes a sequence (corresponding to nucleotides 295-402) of 36 amino acids including the neurokinin A sequence which is identical to the sequence of porcine neuropeptide K.

It can be seen from this that the phE293 insert sequence encodes part of a polypeptide similar, but not identical, to bovine beta-PPT. However, the phE293 insert sequence does not encode the complete sequence of such a polypeptide and apparently lacks at its 5' end a cDNA sequence encoding the 24 amino acid on the N-terminal end of the polypeptide.

In order to be able to complete the sequence of the hPPT, a second cDNA library was constructed, substantially as described above. However, in place of the oligo (dT)$_{12-18}$ primer, the synthetic heptadecamer oligonucleotide probe described above was used as an hPPT-specific primer. Also, instead of using the probe described above, a second synthetic heptadecamer oligonucleotide probe having the sequence

5'GTCGTACCAGTCGGACC-3' was used to probe the clone library. This second probe is complementary to a region close to the 5' end of the insert in phE293 and was used to probe 2,700 transformants. A single strongly positive colony (ph8.216) was identified.

Sequencing of the insert in ph8 216 showed that it contained 260 base pairs, consisting of 113 base pairs in common with and at the 5' end of the insert in phE293 and a further 147 base pairs of sequence, at the 5' end of the common sequence, comprising 66 base pairs encoding the N-terminal amino acids of hPPT and 81 base pairs of 5' untranslated sequence. The sequence for the ph8.216 insert, its corresponding amino acid sequence, and a comparison of these sequences with those for bovine beta-PPT also given in FIG. 1. The ph8.216 insert sequence comprises nucleotides 1 to 260 of the sequence shown in FIG. 1.

From the sequences of the inserts in plasmids phE293 and ph8.216, the complete cDNA sequence encoding hPPT can be derived. This is shown, with the corresponding amino acid sequence, in FIG. 1.

In order that the complete DNA coding for the beta-preprotachykinin might be reconstructed, segments of the cDNA cloned in plasmids ph8.216 and phE293 were excised and ligated using DNA ligase.

Figure 2A:
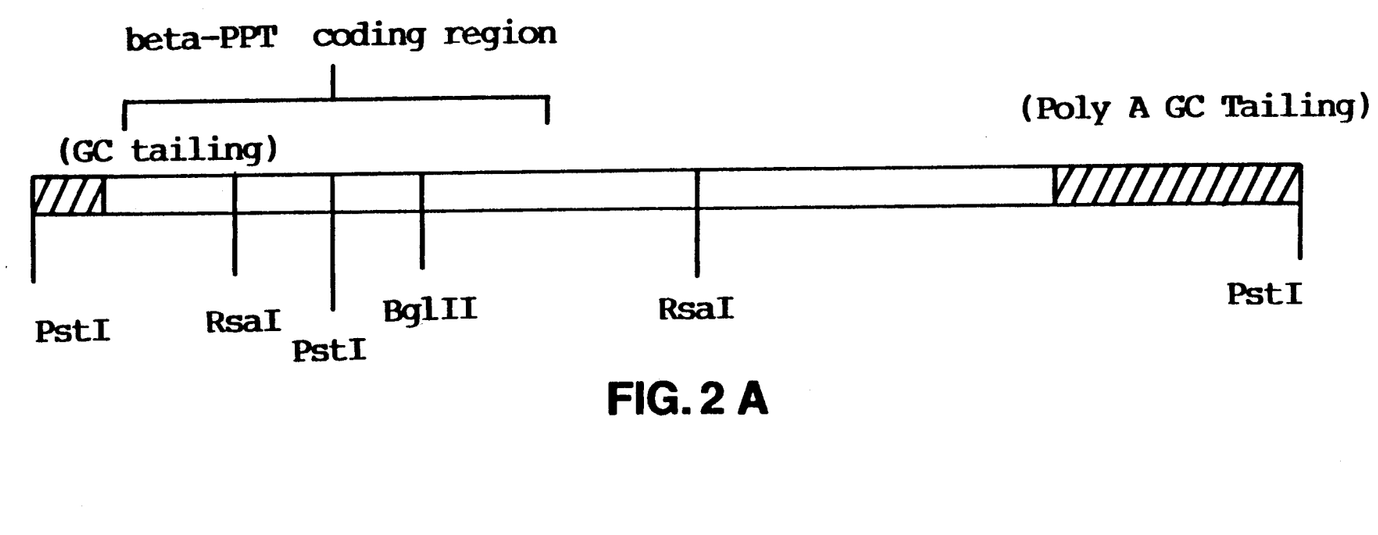
FIGS. 2(a) to (c) shows schematically the restriction enzyme maps of segments excised from 2 plasmids designated 8.216 and E293.
Figure 2B:
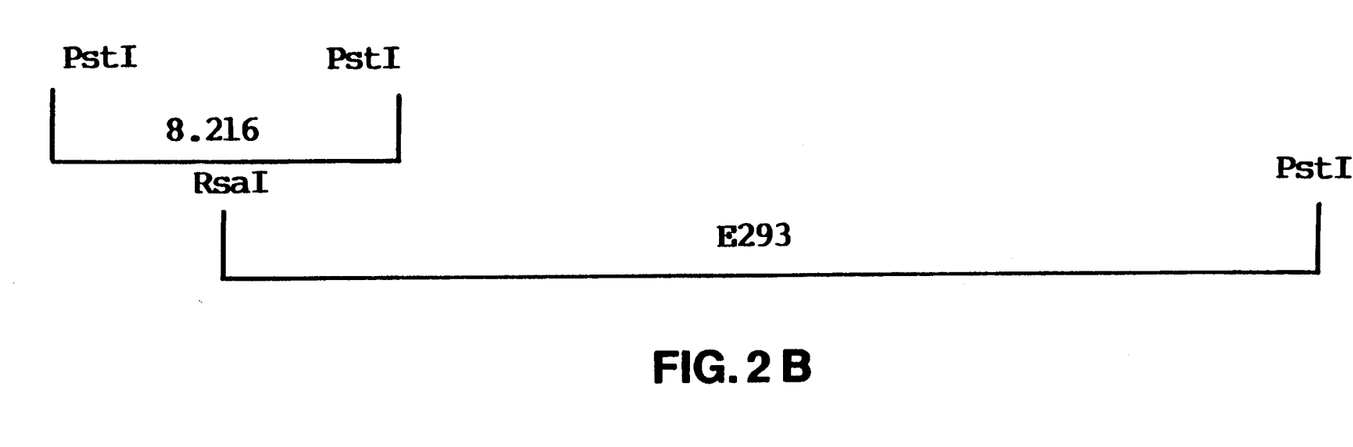
Figure 2C:
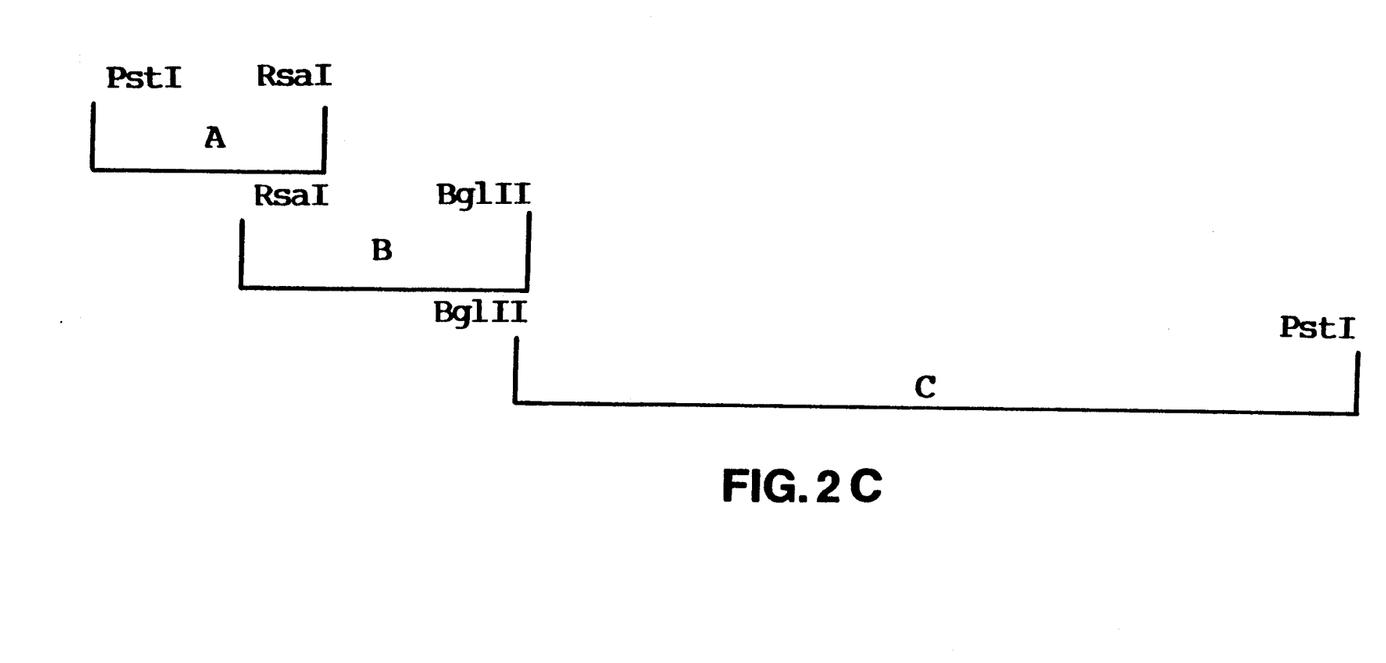

FIG. 2 shows schematically the restriction enzyme maps of the segments excised from the two plasmids 8.216 and E293. One segment (A) was excised from 8.216 and two (B and C) from E293.

The sources of the enzymes referred to in FIG. 2 are (i) Pst I from *Providencia stuartii*; (ii) Rsa I from *Rhodopseudomonas sphaeroides*; and, (iii) Bgl II from *Bacillus globigii* RUB561

Standard genetic engineering procedures, analogous to those described above for the preparation of the two plasmid 8.216 and E293, were employed to excise the desired fragments using restriction endonucleases, to separate the restriction fragments by electrophoresis and to ligate the three fragments to give the recombinant DNA containing the nucleotides 1 to 1021. The vector used for the reconstructed cDNA was M13mp19 DNA cut with PstI.

Restriction enzyme digests of the recombinant confirmed that it contained the complete beta-preprotachykinin DNA.

It has thus been demonstrated that there is a human polypeptide equivalent, but not identical, to bovine beta-PPT. The sequences are over 90% homonologous.

The close similarity between the human and bovine beta-PPT sequences suggests that the human PPT sequence will give rise not only to substance P and neurokinin A but also to other biologically active peptides, such as neuropeptide K.

The discovery by the present inventors of human polypeptide analogous to bovine beta-PPT is of considerable significance in both the research and clinical environments. Using the CDNA sequence, it will be possible to develop probes for mRNA encoding the biologically active peptides contained in human PPT. This will enable researchers to localise and quantitate productions in the body of the biologically active peptides.

The cloning and expression of human PPT mRNA or parts thereof encoding the biologically active peptides will enable production of the polypeptide or the peptides in sufficient quantity to carry out determinations of their pharmacological effects and to produce them for use as pharmaceuticals. For instance, it is envisaged that human neuropeptide K may be of use in pain control and as an anti-inflammatory agent.

The ability to produce the polypeptide or parts thereof in quantity also could be used to develop radioimmunoassays for the polypeptide or the parts thereof. Such assays would be of use, for instance, in the measurement of circulating levels of the peptides derived from human PPT. Such an assay would be useful in the diagnosis of carcinoid syndrome or in monitoring the success of surgical or medical procedures for control of this condition.

The present discovery may also enable the production of tailored peptides similar to, but more effective than, the known peptides.

Other products and applications of the teaching of this invention will be readily apparent to those skilled in the art, and such products and applications also fall within the scope of this invention. Thus, the present invention is based on the discovery of the existence of human PPT and the elucidation of its mRNA DNA coding sequence and its amino acid sequence.

It will of course be understood that the present invention has been described above purely by way of example, and modifications of detail can be made within the scope of the invention.

We claim:

1. The polypeptide, beta-preprotachykinin (111–126), having the amino acid sequence:

Ala—Leu—Asn—Ser—Val—Ala—Tyr—Glu—Arg—Ser—Ala—Met—Gln—Asn—Tyr—Glu.

2. A pharmaceutical preparation containing as active principle a polypeptide claimed in claim 1 in combination with a pharmaceutical carrier.

* * * * *